United States Patent [19]

Philion et al.

[11] Patent Number: 5,693,673
[45] Date of Patent: *Dec. 2, 1997

[54] PROCESS OF PREPARING 2,2'-(1-METHYL-1,2-ETHANEDIYLIDENE)BIS[HYDRAZINE CAROXIMIDAMIDE]

[75] Inventors: Richard Philion, Pottstown; Steven A. Elenbaas, Phoenixville, both of Pa.

[*] Notice: The term of this patent shall not extend beyond the expiration date of Pat. No. 5,659,083.

[73] Assignee: Sanofi, Paris Cedex

[21] Appl. No.: 655,518

[22] Filed: May 30, 1996

[51] Int. Cl.$^6$ .................... A61K 31/155; C07C 277/08; C07C 279/00
[52] U.S. Cl. ............................................ 514/632; 564/227
[58] Field of Search ............................ 564/227; 514/632

[56] References Cited

U.S. PATENT DOCUMENTS 3,355,491  11/1967  Nilcs et al. .................... 260/564
4,520,031  5/1985  Knight ............................ 514/632

OTHER PUBLICATIONS

Baiocchi et al, J. Med. Chem, 6, 431 (1963).
Oliverio et al, J. Pharm. Sci., 52, 202 (1963).

*Primary Examiner*—Peter O'Sullivan
*Attorney, Agent, or Firm*—William J. Davis; Imre Balogh; Paul E. Dupont

[57] ABSTRACT

Process for the preparation of 2,2'-(1-methyl 1,2-ethanediylidene)bis[hydrazine carboximidamide] by:
a) reacting aminoguanidine hydrochloride with methylglyoxal aldehyde or methylglyoxal dimethyl acetal; and
b) purifying the 2,2'-(1-methyl-1,2-ethanediylidene)bis[hydrazine carboximidamide] by crystallization from an acidic aqueous-isopropyl alcohol medium.

6 Claims, No Drawings

PROCESS OF PREPARING 2,2'-(1-METHYL-1,2-ETHANEDIYLIDENE)BIS[HYDRAZINE CAROXIMIDAMIDE]

BACKGROUND OF THE INVENTION

1. Field of the Invention

The present invention relates to a process of preparing 2,2'-(1-methyl-1,2-ethanediylidene)bis[hydrazine carboximidamide] having greatly reduced impurities therein useful in a method of treating cancer or advanced malignant diseases.

2. Reported Developments

The compound 2,2'-(1-methyl-1,2-ethanediylidene)bis [hydrazine carboximide] is known by several names, such as 1,1'[(methylethanediylidene)dinitrilo] diguamidine, pyruvaldehyde bis (amidinohydrazone), mitoguazone and methylglyoxal bis-guanylhydrazone, methyl GAG or MGBG, represented by the formula

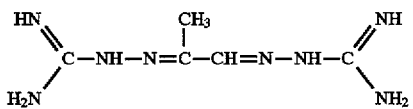

MGBG and its salts have been disclosed in the prior art since the 1950s for use against various diseases as illustrated by the following patents and publications.

The antitumor activity of MGBG in leukemia-L1210- and adenocarcinoma-755-bearing rodents was first reported by Freelander et al, 18 Cancer Res. 360 (1958).

Japanese 51044643 discloses MGBG and its acid addition salts as effective agents against virus diseases of fishes to prevent and treat infections, pancreatic necrosis and hematopoietic necrosis.

Japanese 50029520 discloses MGBG and its salts for use against influenza virus.

U.S. Pat. No. 4,201,788 discloses MGBG for the treatment of non-malignant proliferative skin diseases.

MGBG is known to inhibit S-adenosylmethionine decarboxylase (SAMD), which is a key enzyme in polyamine synthesis, leading to cellular polyamine depletion. However, investigations with MGBG revealed unacceptable levels of toxicity. The toxicological effects of MGBG observed, some of which are peculiar to certain animal species, include gastrointestinal toxicity, delayed and fatal hypoglycemia, hepatic and renal damage, bone marrow depression, diarrhea and phlebitis. These effects have also prevailed in human subjects undergoing MGBG treatment. Additionally, several toxic effects were demonstrated which are unique to man. These include esophagitis, ulcerative pharyngitis, laryngitis, stomatitis, genital mucosa swelling, conjunctivitis, mucositis, erythema, edema, desquamating dermatitis, and profound anorexia with associated weight loss. Patients who were administered MGBG on a daily schedule exhibited remission to acute leukemia only after a precarious struggle with the oftentimes life threatening side effects. In many patients, treatment had to be discontinued before any beneficial results could be noted.

Knight et al in *Can. Treat. Rep.*, 63 1933–1937 (1979) found that the levels of toxicity were dose schedule related and could be controlled. U.S. Pat. No. 4,520,031 addresses the issue of such dose schedule related control in order to reduce toxicity.

The dose schedule control, as described in the patent was based on the postulation that MGBG exerts an inhibitory action relative to polyamine biosynthesis. Physiologically achievable effects of MGBG may be related to the inhibition of the enzyme S-adenosyl methionine decarboxylase, which catalyses the synthesis of the polyamine, spermidine.

Spermidine is believed to play an important role in the initiation of DNA synthesis. Studies have shown that MGBG-mediated depression of DNA synthesis is associated with spermidine depletion and putrescine accumulation.

Another area in which polyamines are believed to play a major role is in RNA synthesis, especially that of transfer (t) RNA. The methylation of tRNA may be directly stimulated by polyamines, a finding of particular interest in light of the reports that neoplastic tissue differs from normal tissue with respect to the extent of methylated tRNA. Here, too, spermidine appears to play a critical role.

Polyamine accumulation appears to be a necessary requisite to DNA synthesis at an optimal rate, in both normal and neoplastic tissues. Thus, the toxicity of MGBG observed in tissues with rapid turnover (skin, G.I. mucosa and bone marrow) may be directly related to inhibition of polyamine biosynthesis and a subsequent depletion of RNA and DNA, the agents which ultimately regulate cell replication. There is, however, strong evidence that: (1) polyamines are excreted in excess in the majority of cancer patients; (2) polyamines, especially spermidine, are released from tumor cells during and after effective chemotherapy, with an initial peak in excretion and in serum levels and subsequent drop toward normal values; and (3) chemotherapy which produces only bone marrow (or other normal tissue) toxicity, and is without antitumor effectiveness, does not produce a significant increase in polyamine excretion. The latter observation would suggest either that cancer cells have much higher levels of polyamines than normal cells, even those with higher rates of DNA synthesis, or that therapy which is effective produces rather specific effects on polyamine synthesis in cancer cells. Thus, the depletion of spermidine is associated with the action of MGBG.

In studies conducted on men, toxicological effects observed clinically have been attributed to cumulative effects of repeated daily doses. This cumulation or accretion of toxicity is possibly explained by the unusually prolonged period required for urinary elimination of MGBG in man. Bioavailability studies in man with MGBG-$C^{14}$ have shown that following a single intravenous infusion over a period of 20 minutes, the radioactivity rapidly disappeared from the plasma and that over an extended period of 3 weeks approximately 60 percent of the drug was excreted unchanged in the urine. These data suggest that MGBG accumulates in the tissues and is slowly leached from tissue deposits to accomplish elimination.

The patentee, after considerably large number of studies conducted with MGBG in the treatment of various tumors, concludes that a weekly schedule of administration is most effective in achieving a higher therapeutic index while reducing toxicity to an acceptable level. Accordingly, a dose range of from 250 mg/m$^2$ to 1000 mg/m$^2$ of MGBG administered at weekly intervals was established for the treatment of various tumors.

While the above-indicated dose range decreases toxicological side effects and affords treatments of various tumors, long term accumulation of MGBG is still a problem requiring further studies and/or treatment modifications.

Applicants have conducted extensive studies of MGBG with the object to further reduce toxic side effects thereof. In the course of their studies it was discovered that MGBG contains relatively large mounts of impurities which may contribute to the toxicological side effects of MGBG. Accordingly, great efforts were expended to identify and reduce the amount of impurities present in MGBG and its salts.

The process of preparing guanylhydrazones is described by Baiocchi et al., *J. Med. Chem.*, 6, 431 (1963) and Oliverio, Denham, *J. Pharm. Sci.*, 52, 202 (1963).

The process comprises reacting of an aminoguanidine salt with the corresponding carbonyl compound in an aqueous or aqueous-alcohol medium in the presence of a catalytic amount of acid.

The process uses commercially available aminoguanidine bicarbonate and is described as follows.

General Preparation of Guanylhydrazones

To a solution of 0.11 mole (15 g) of aminoguanidine bicarbonate in 125 mL of water was added slowly to the desired acid (a few drops of amyl alcohol was added in order to prevent foaming) until the pH of the solution was less than 7. The solution was filtered from trace amounts of insoluble solids. The appropriate carbonyl compound was then added to the slightly acid filtrate at ca 60° C. The amount of carbonyl compound used was such that the ratio of aminoguanidine per carbonyl function was 1:1. If the carbonyl compound did not dissolve in the aqueous mixture, ethanol was added until the reaction mixture was homogeneous. The solution was then stirred at room temperature for 16 hours. If a precipitate was formed the solid product was isolated by filtration. Otherwise the reaction mixture was evaporated until a solid residue was obtained using methanol, ethanol and a combination of solvents.

Recovery of guanylhydrazones was low.

In addition of low yield we have found that the products contained relatively large amounts of impurities.

Experimental

We have developed methods for analysis of mitoguazone dihydrochloride using various systems to identify and quantify its impurities. One system of analysis included High Performance Liquid Chromatography. Considered in terms of determining chromatographic impurity levels, a high degree of specificity provides confidence that all the potential species of interest are detectable. Where these species, including process impurities and degradation products, are not available to inject directly onto the chromatographic system, specificity testing is usually conducted on stressed samples using one or more techniques which can usually be placed in one of two broad categories:

(a) Use of a specialized detection system to extract further information from the analyte peak.

(b) Some form of comparison between complimentary separation techniques, the first being the system under validation and the second being a system which, by virtue of its differing selectivity, might be expected to resolve species co-eluting in the first instance.

Examples of techniques in the first category include the use of diode array and mass spectroscopy detectors to obtain UV/Visible or mass spectra respectively from various positions through the analyte peak allowing, potentially, for the detection of co-eluting species. Techniques in the second category include the use of flow switching apparatus to divert the analyte peak onto a second stationary phase with a different selectivity, or comparison of results from the system being validated with those from a second chromatographic technique such as Thin Layer chromatography (TLC).

Equipment and Chemicals

HPLC data were generated using various Kontron (Watford, Herts) and Waters (Watford, Herts) pump, autosampler, column oven and detector models. HPLC data were processed using Multichrom™ V1.8–2 (LabSystems, Altringham, Cheshire). UV/visible absorption spectra were captured using an HP 1040 diode array detector (Hewlett Packard, Bracknell, Berks.). Light stressing (Xenon source, filtered through window glass) was performed in a Haraeus Suntest™ (Alplas Technology, Oxford). HPLC grade acetonitrile was obtained from Rathburn chemicals (Walkerburn, Scotland), HPLC grade heptane sulphonic acid (sodium slat), and inorganic chemicals were obtained from BDH limited (Poole, Dorset). ACVA (4,4'-Azobis(4-cyanovaleric acid), a radical initiator, exposure to which mimics oxidative stress, was obtained from Aldrich (Gillingham, Dorset). Mitoguazone dihydrochloride and purified water were obtained in-house.

Stress Sample Preparation

Samples of mitoguazone dihydrochloride (approximately 370 mg, equivalent to 250 mg base) were accurately weighed into 50 mL volumetric flasks and stressed according to the conditions given below. Stressing was continued for a maximum of 7 days or until 20 to 50% degradation had been achieved. After stressing, samples were neutralized, if necessary, and diluted to volume with purified water to give ~5 mg(base)/mL solutions for TLC analysis. Aliquots of these solutions were diluted with purified water to give ~1 mg(base)/mL solutions for use in impurity determinations by HPLC. Finally, aliquots of these solutions were either diluted in HPLC mobile phase to give ~0.01 mg(base)/mL solutions for HPLC assay.

Stress Conditions

Heat: Sample held at 80° C. for 7 days. Acidic: 10 mL of 0.1M hydrochloric acid was added to the sample and the solution held at 70° C. for 7 days. Basic: 10 mL of 0.1M sodium hydroxide was added to the sample and the solution held at 70° C. for 2 days. Aqueous: 10 mL of purified water was added to the sample and the solution held at 70° C. for 7 days. Oxidative: 10 mL of a 0.1M aqueous ACVA solution was added and the sample held at 40° C. for 7 days. Light: Sample received an overall illumination of ~15,000 klx hours (with associated UV). Assay: Samples were chromatographed isocratically on a 25 cm×0.46 i.d. Hypersil BDS C8 5 μm columns (Anachem, Luton, Beds.) using a mobile phase consisting of 0.05M potassium dihydrogen orthophosphate buffer containing 1 g/L of heptane sulphonic acid (sodium salt) and adjusted to pH 3.0 with concentrated orthophosphoric acid (89% by volume) and acetonitrile (11% by volume). The flow rate was 2 mL/minute, the detector wavelength was 283 nm, the injection volume was 20 μL and column temperature was 40° C. Samples were quantified with respect to an accurately prepared external standard (nominally 0.01 mg(base)/mL. Impurity Method: Chromatographic conditions were as for the assay except a detector wavelength of 210 nm was used. A second HPLC system was used with an aqueous to acetonitrile mobile phase ratio of 85% to 15% by volume, primarily to estimate specific process impurities. Impurities were quantified with respect to an accurately prepared external standard (nominally 0.005 mg(base)/mL).

TLC Method

20 μL of each sample was spotted onto a silica gel TLC plate (Merck 60F$_{254}$). The plate was developed to a height of 10 cm in an acetone/ammonium hydroxide (SG 0.88)/water (90:5:5% by volume) mobile phase. Impurities were estimated against dilute mitoguazone dihydrochloride spots, both under short wavelength ultraviolet light (254 nm), and following treatment with a nitroprusside (sodium)-ferricyanide spray reagent.

Results

Triplicate samples representing 0, 80%, 100% and 120% of the nominal mitoguazone dihydrochloride concentration were analyzed. The results obtained are given in Table I

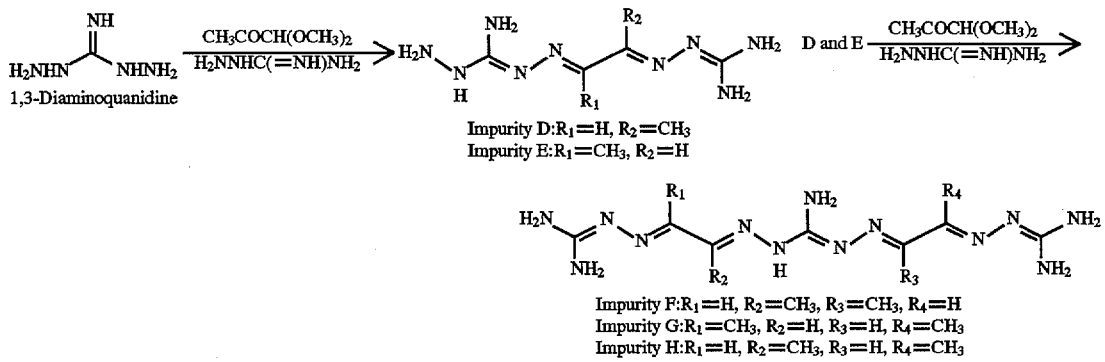

Impurity D: $R_1=H$, $R_2=CH_3$
Impurity E: $R_1=CH_3$, $R_2=H$

Impurity F: $R_1=H$, $R_2=CH_3$, $R_3=CH_3$, $R_4=H$
Impurity G: $R_1=CH_3$, $R_2=H$, $R_3=H$, $R_4=CH_3$
Impurity H: $R_1=H$, $R_2=CH_3$, $R_3=H$, $R_4=CH_3$

TABLE I

Recovery Data

HPLC DATA*

| Sample Identity | % nominal added | % nominal recovered |
|---|---|---|
| Blank 1 | 0 | 0 |
| Blank 2 | 0 | 0 |
| Blank 3 | 0 | 0 |
| 80% 1 | 81.1 | 81.0 |
| 80% 2 | 80.9 | 80.4 |
| 80% 3 | 83.6 | 83.3 |
| 100% 1 | 101.5 | 101.6 |
| 100% 2 | 103.6 | 103.5 |
| 100% 3 | 104.6 | 104.2 |
| 120% 1 | 122.3 | 121.3 |
| 120% 2 | 121.9 | 122.5 |
| 120% 3 | 119.0 | 118.8 |

HPLC Assays*. Least Squares Regression Analysis of the data gave an average accuracy of 99.8% (Coefficient of Correlation 0.99935).

Analysis of Stressed Samples

Stressed samples were assayed by HPLC whilst chromatographic impurity levels were determined by HPLC and TLC. The chromatographic data are summarized in Table II.

TABLE II

Chromatographic Assay and Impurity Data for Stressed Mitoguazone Dihydrochloride

| Stress Condition | HPLC Assays (% w/w) | Impurities by HPLC (% w/w) | Impurities by TLC (% w/w) |
|---|---|---|---|
| Control | 100.6, 99.9 | 1.3 | <0.7 |
| Heat | 100.1, 100.2 | 1.1 | <1.1 |
| Acidic | 87.6, 87.0 | 14.0 | <12.5 |
| Basic | 74.9, 75.4 | 27.9 | <25.3 |
| Aqueous | 69.4, 69.1 | 31.9 | <29.5 |
| Oxidative | 93.7, 94.5 | 6.5 | <5.8 |
| Light | 99.9, 99.2 | 1.4 | <0.7 |

Using HPLC, TLC and mass spectroscopy, impurities contained in the starting materials or formed during the process of making the final product were identified and quantified.

We have found that the diaminoguanidine related impurities account for more than 70% of the total MGBG-dihydrochloride impurity level.

The general reaction scheme for the production of the impurities and their chemical names follows.

wherein
D=[2-[(Aminoiminomethyl)hydrazono]propylidene]-carbonimidic dihydrazide.
E=[2-[(Aminoiminomethhyl)hydrazono]-1-methylethylidene]-carbonimidic dihydrazide.
F=Bis[2-[(Aminoiminomethyl)hydrazono]-1-methylethylidene]-carbonimidic dihydrazide.
G=Bis[2-[(Aminoiminomethyl)hydrazono]propylidene]-carbonimidic dihydrazide.
H=[2-[(Aminoiminomethyl)hydrazono]-1-methylethylidene][2-[(aminoiminomethyl)hydrazono]propylidene]-carbonimidic dihydrazide.

In copending application D.N. 70493, Ser. No. 08/655,512 now 5657883 filed of even date with the present application, reaction parameters were studied and modified in order to reduce impurities in the final product. Said copending application which is incorporated by reference in its entirety, discloses a process for the preparation of 2,2-'-(1-methyl-1,2-ethanediylidene)bis[hydrazine carboximidamide] comprising the steps of:

a) removing impurities from aminoguanidine bicarbonate by suspending aminoguanidine bicarbonate in water and filtering the suspension;

b) reacting the filtered aminoguanidine bicarbonate with methylglyoxal dimethyl acetal in an aqueous reaction medium to produce 2,2'-(methyl-1,2-ethanediylidene)bis[hydrazine carboximidamide]; and c) purifying the 2,2'-(1-methy-1,2-ethanediylidene)bis[hydrazine carboximidamide] by recrystallization from an acidic aqueous-isopropanol medium.

An essential step in the process is the removal of the impurities from the aminoguanidine bicarbonate starting material by suspending aminoguanidine bicarbonate in water and filtering out the impurities from the suspension.

We have now discovered that instead of using aminoguanidine bicarbonate as a starting material, aminoguanidine hydrochloride may be used to react with methylglyoxal dimethyl acetat in an aqueous reaction medium to produce 2,2'-(1-methyl-1,2-ethanediylidene)bis[hydrazine caroximidamide]. The process which includes a subsequent purification step provides a final product which is at least 99.5% pure.

SUMMARY OF THE INVENTION

The process of obtaining highly purified 2,2'-(1-methyl-1,2 ehanediylidene)bis[hydrazine carboximidamide]

involves reacting aminoguanidine hydrochloride with methylglyoxal dimethyl acetal which comprises the steps of:

a) dissolving one part aminoguanidine hydrochloride in a mixture of about 0.5 to 3 parts, preferably in about 0.93 parts, of water and about 0 to 3 parts of a water miscible organic solvent, preferably about 0.75 parts of isopropyl alcohol;

b) adjusting the pH of the solution to about 0 to 5, preferably about 0 to 1 with concentrated hydrochloric acid;

c) adding to the solution about 0.25 to 1 parts of methylglyoxal aldehyde, preferably about 0.5 parts of methylglyoxal dimethyl acetal, at a temperature of about 0° to 50° C., preferably at 25° to 30° C.;

d) stirring the reaction mixture for about 1 to 48 hours, preferably for about 1 to 16 hrs at ambient temperature;

e) adding about 0.5 to 20 parts of a water miscible organic solvent, preferably about 5 parts of isopropyl alcohol, to the reaction mixture to produce the solid 2,2'-(1-methyl-1,2 ethanediylidene)bis[hydrazine carboximidamide];

f) collecting the solid crude 2,2'-(1-methyl-1,2-ethanediylidene)bis[hydrazine carboximidamide] by filtration and washing the same with 1 to 10 parts of an organic solvent, preferably with 1 to 2 parts of isopropyl alcohol; and g) optionally drying the crude final product before purification in a 45° C. vacuum oven.

The purification process of the crude 2,2'-(1-methyl-1,2-ethanediylidene)bis[hydrazine carboximidamide] comprises the steps of:

h) dissolving the crude compound in about 0.5 to 4 parts of deionized water, preferably in about 2 parts of deionized water;

i) adding about 0.5 to 2 parts of a water miscible organic solvent, preferably about 1 part of isopropanol;

j) adjusting the pH of the solution to about 0 to 5, and preferably to 0 to 1 with concentrated hydrochloric acid;

k) stirring the solution for about 0.5 to 2 hours while adding 0.1 to 2 parts of deionized water and maintaining the temperature of the solution at about 28°-32° C.;

l) filtering the solution to remove insoluble impurities;

m) adding to the filtered solution about 0.5 to 10 parts of a water miscible organic solvent, preferably about 5 parts of isopropyl alcohol to precipitate the compound;

n) cooling the mixture to about 0° to 25° C., preferably to about 10° C.;

o) collecting the solid product by filtration and washing the filtrate with 0.5 to 10 parts of an organic solvent, preferably with one part of isopropyl alcohol; and p) drying the purified product.

DETAILED DESCRIPTION OF THE INVENTION

As used herein the process of synthesizing and purifying 2,2'-(1-methyl-1,2-ethanediylidene)bis[hydrazine carboximide] also relates to and includes synthesis and purification of its various forms including its hydrochloride monohydrate, dihydrate and hemihydrate forms.

In the process of synthesizing and purifying 2,2'-(1-methyl-1,2-ethanediylidene)bis[hydrazine carboximidamide] we prefer to use isopropyl alcohol. However, other water miscible organic solvents which may be used include methanol, ethenol, n-propyl alcohol, tetrahydrofuran, acetic acid, dimethyl formamide, acetonitrile and dimethyl sulfoxide or mixtures thereof.

Aminoguanidine hydrochloride, methylglyoxal aldehyde and methylglyoxal dimethyl acetal are available commercially, such as from Aldrich Chemical Co., and they can also be made by processes known in the art.

A representative example (Example 1) of synthesizing and purifying 2,2'-(1-methyl-1,2-ethanediylidine)bis [hydrazine carboximidamide] illustrate the invention.

EXAMPLE 1

(A) Synthesis 60.0 grams of aminoguanidine hydrochloride was dissolved in 56 milliliters of deionized water and 36 grams of isopropyl alcohol. The pH of the solution was adjusted to about 0 to 1 by adding concentrated hydrochloric acid. 30.96 grams of methylglyoxal dimethylacetal was added over 1.5 to 3 hours while maintaining the reaction temperature between 25° and 30° C. The reaction mixture was then stirred at ambient temperature for an additional 16 hours. 240 grams of isopropyl alcohol was added and the reaction mixture was cooled to 10° C. The crude product which formed during the reaction process was collected by filtration and was washed with 90 milliliters of isopropyl alcohol. The washed filtrate was then dried in a 45° C. oven over night. The yield was 87% of the theoretical yield.

(B) Purification 79.3 grams of the crude product obtained in (A) was dissolved in 159 grams of deionized water at 35° C. 60.7 grams of isopropyl alcohol was added to the solution and the pH was adjusted to 0–1 by adding concentrated hydrochloric acid. The pH adjusted solution was stirred for 1 hour while maintaining its temperature at 28°–32° C. and adding 10 milliliters of deionized water. The mixture was filtered to remove impurities, such as mechanical dirt particles. 312 grams of isopropyl alcohol was then added to the solution to precipitate the product. The mixture containing the precipitated product was cooled to between 8°–12° C. and stirred for abut 15 minutes. The purified product was then washed with 68 milliliters of isopropyl alcohol and dried in a 45° C. vacuum oven.

The yield of the purified product was 67.5% of the theoretical yield.

Samples of purified 2,2'-(1-methyl-1,2-ethanediylidine) bis[hydrazine carboximidamide] produced by: 1.) reacting aminoguanidine bicarbonate with methylglyoxal dimethyl acetal or 2.) reacting aminoguanidine hydrochloride with dimethylglyoxal dimethyl acetal were analyzed by HPLC. Comparative results are shown in Table II and Table III.

TABLE II

Assay Results For Lots of Aminoguanidine Bicarbonate Used in Production of MGBG and Assay Results of MGBG Produced Therewith.

| MGBG Lots Produced From Aminoguanidine Bicarbonate | Impurities (1,3-diaminoguanidine) by HPLC % w/w | MGBG ETI by HPLC Area % |
|---|---|---|
| L-1 | 1.0 | 1.73 |
| L-2 | 0.54 | 0.77 |
| L-3 | 0.38 | 0.65 |
| L-4 | 0.2 | 0.60 |
| L-5 | 0.2 | 0.64 |
| L-6 | 0.2 | 0.44 |

TABLE III

Assay Results For Lots of Aminoguanidine Hydrochloride Used in Production of MGBG and Assay Results of MGBG Produced Therewith

| MGBG Lots Produced From Aminoguanidine Hydrochloride | Impurities (1,3-diamino-guanidine) by HPLC % w/w | MGBG ETI by HPLC Area % |
| --- | --- | --- |
| L-7 | none detected | 0.07 |
| L-8 | none detected | 0.04 |

Aminoguanidine hydrochloride was found to contain lower levels of impurities than aminoguanidine bicarbonate and gave a superior quality MGBG. Purity of MGBG produced by the use of aminoguanidine hydrochloride and according to the present invention was found to be as high as 99.9%. Such highly pure MGBG is well-suited for pharmaceutical compositions for the treatment of cancer and other diseases.

The invention has been described in detail with particular reference to certain preferred embodiments thereof, but it will be understood that variations and modifications can be effected within the spirit and scope of the invention.

What is claimed is:

1. A process for preparing 2,2'-(1-methyl-1,2-ethanediylidene)bis[hydrazine carboximidamide] comprising the steps of:
   a) dissolving one part aminoguanidine hydrochloride in a mixture of about 0.5 to 3 parts of water and about 0 to 3 parts of a water miscible organic solvent;
   b) adjusting the pH of said solution to about 0 to 5 with concentrated hydrochloric acid;
   c) adding to the solution about 0.25 to 1 parts of methylglyoxal aldehyde or methylglyoxal dimethyl acetal at a temperature of about 0° to 50° C. to obtain a reaction mixture;
   d) stirring the reaction mixture for about 1 to 48 hours at ambient temperature;
   e) adding to the reaction mixture about 0.5 to 20 parts of a water miscible organic solvent to produce the solid crude 2,2'-(1-methyl-1,2-ethanediylidene)bis[hydrazine carboximidamide];
   f) collecting the crude 2,2'-(1-methyl-1,2-ethanediylidene)bis[hydrazine caroximidamide] by filtration and washing it with 1 to 10 parts of an organic solvent;
   g) dissolving the crude 2,2'-(1-methyl-1,2 ethanediylidene)bis[hydrazine carboximidamide] in about 0.5 to 4 parts of water;
   h) adding to the solution about 0.5 to 2 parts of a water miscible organic solvent;
   i) adjusting the pH of the solution to about 0 to 5;
   j) stirring the solution for about 0.5 to 2 hours while adding about 0 to 2 parts of water and maintaining the temperature of the solution at about 28° to 32° C.;
   k) adding to the solution about 0.5 to 10 parts of a water miscible organic solvent to precipitate 2,2'-(1-methyl-1,2-ethanediylidene)bis[hydrazine carboximidamide];
   l) cooling the mixture to about 0° to 25° C.;
   m) collecting the solid 2,2'-(1-methyl-1,2,-ethanediylidene)bis[hydrazine carboximidamide] by filtration and washing it with 0.5 to 10 parts of an organic solvent; and
   n) drying the purified 2,2'-(1-methyl-1,2-ethanediylidene)bis[hydrazine carboximidamide].

2. 2,2'-(1-methyl-1,2-ethanediylidene)bis[hydrazine carboximidamide] prepared by the process of claim 1.

3. A method of treating cancer or malignant diseases in a mammal comprising: administering to said mammal an effective amount of a pharmaceutical composition containing the compound of claim 2.

4. A process for preparing 2,2'-(1-methyl-1,2-ethanediylidene)bis[hydrazine carboximidamide] comprising the steps of:
   a) dissolving one part of aminoguanidine hydrochloride in a mixture of about 0.93 parts of water and about 0.75 parts of isopropyl alcohol;
   b) adjusting the pH of the solution to about 0 to 1 with concentrated hydrochloric acid;
   c) adding to the solution about 0.5 parts of methylglyoxal dimethyl acetal at a temperature of 25° to 30° C.;
   d) stirring the solution for about 1 to 16 hrs at ambient temperature;
   e) adding about 5 parts of isopropyl alcohol to the reaction mixture to produce the solid 2,2'-(1-methyl-1,2-ethanediylidene)bis[hydrazine carboximidamide];
   f) collecting the solid crude 2,2'-(1-methyl-1,2-ethanediylidene)bis[hydrazine carboximidamide] by filtration and washing it with 1 to 2 parts of isopropyl alcohol;
   g) dissolving the crude 2,2'-(1-methyl-1,2-ethanediylidene)bis[hydrazine carboximidamide] in about 2 parts of water;
   h) adding about one part of isopropyl alcohol;
   i) adjusting the pH of the solution to 0 to 1 with concentrated hydrochloric acid;
   j) stirring the solution for about 0.5 to 2 hours while adding 0 to 2 parts of water and maintaining the temperature of the solution at about 28°–32° C.;
   k) filtering the solution to remove insoluble impurities therefrom;
   l) adding to the filtered solution about 5 parts of isopropyl alcohol to precipitate the 2,2'-(1-methyl-1,2-ethanediylidene)bis[hydrazine carboximidamide];
   m) cooling the mixture to about 10° C.;
   n) collecting the solid 2,2'-(1-methyl-1,2-ethanediylidene)bis[hydrazine carboximidamide] by filtration and washing it with one part of isopropyl alcohol; and
   o) drying the 2,2'-(1-methyl-1,2-ethanediylidene)bis[hydrazine carboximidamide].

5. 2,2'-(1-methyl-1,2-ethanediylidene)bis[hydrazine carboximidamide] prepared by the process of claim 4.

6. A method of treating cancer or malignant diseases in a mammal comprising: administering to said mammal an effective amount of a pharmaceutical composition containing the compound of claim 5.

* * * * *